United States Patent [19]
Wu et al.

[11] Patent Number: 5,202,173
[45] Date of Patent: Apr. 13, 1993

[54] ULTRA SOFT CLOTH-LIKE EMBOSSED PLASTIC FILM HAVING POST-EMBOSSED STRETCHED AREAS

[75] Inventors: Pai-Chuan Wu, Cincinnati, Ohio; Thomas R. Ryle, Burlington, Ky.; Robert M. Mortellite, Hamilton; J. David Toppen, Loveland, both of Ohio

[73] Assignee: Clopay Corporation, Cincinnati, Ohio

[21] Appl. No.: 821,342

[22] Filed: Jan. 13, 1992

Related U.S. Application Data

[63] Continuation of Ser. No. 478,935, Feb. 12, 1990, abandoned.

[51] Int. Cl.$^5$ .......................... B32B 5/14; B32B 3/30
[52] U.S. Cl. .................................. 428/131; 428/156; 428/170; 428/174; 428/167; 428/179; 428/213; 428/141; 428/500; 428/910; 264/289.3; 264/288.8
[58] Field of Search .............. 428/156, 170, 174, 167, 428/174, 213, 141, 131, 500, 910; 264/289.3, 288.8

[56] References Cited

U.S. PATENT DOCUMENTS

| | | | |
|---|---|---|---|
| 3,484,835 | 12/1969 | Trounstine et al. | 161/130 |
| 4,029,264 | 6/1977 | Reese | 206/397 X |
| 4,153,664 | 5/1979 | Sabee | 264/288.8 X |
| 4,223,063 | 9/1980 | Sabee | 428/224 |
| 4,376,147 | 3/1983 | Byrne et al. | 428/167 |
| 4,546,029 | 10/1985 | Cancio et al. | 428/141 |
| 4,859,519 | 8/1989 | Cabe, Jr. et al. | 428/131 |

Primary Examiner—Ellis P. Robinson
Assistant Examiner—William P. Watkins, III
Attorney, Agent, or Firm—Wood, Herron & Evans

[57] ABSTRACT

An embossed plastic film is made ultra soft and cloth-like by providing a plurality or post-embossed stretched areas along lines that are spaced uniformly across its width and length. The stretched areas are thinner than the unstretched areas. Films also have unique textures and offer cloth-like or non-woven appearances.

14 Claims, 2 Drawing Sheets

ULTRA SOFT CLOTH-LIKE EMBOSSED PLASTIC FILM HAVING POST-EMBOSSED STRETCHED AREAS

This application is a continuation of application Ser. No. 478,935, filed Feb. 12, 1990 now abandoned.

BACKGROUND OF THE INVENTION

Beginning several decades ago, plastic film began to achieve wide spread use in the fabrication of many useful articles, quite often as a replacement for woven fabrics. Early in the development of plastic film as a substitute for woven fabrics, patterns were created by imposing the image of a woven fabric into a film during the process of making the film. Wire screens, along with other mechanical implements, were later employed to create plastic films having various designs. As technology developed, metal rolls having engraved patterns were employed in the production of embossed plastic films which would simulate various designs. During this period of time, the person of ordinary skill in the art who made useful articles from plastic film, typically disposable diapers, covers, water repellent clothing, and the like, worked with the film on machinery and observed or studied its characteristics. Refinements or adjustments in the machinery as well as the material took place in order to produce useful articles from such embossed plastic films on high speed production machinery.

U.S. Pat. No. 3,484,835 which issued in 1969 is directed to a plastic film embossed with a pattern simulating a woven taffeta design and the film had an especially desirable characteristic of edge curl resistance during machine processing into useful articles. Embossed plastic film disclosed in this patent offered significant improvement over the earlier taffeta design which existed in the prior art. The simulated taffeta design disclosed in the above mentioned patent is only an example of many different designs created and employed by film fabricators in their effort to simulate woven fabrics or achieve other various visual appearances and physical properties which were advantageous from a manufacturing or consumer standpoint.

Another one of such many designs is referred to in the art as a matte finish. A matte finish has heretofore been characterized by a rather dull finish on a plastic film with no visually perceptible pattern. Matte finishes have been produced in films by the employment of sand-blasted embossing rollers. With the advancement of technology including new formulations in polymer compositions of the polyolefin type, particularly polyethylene, polypropylene and polybutadiene and their copolymers, the problem of handling various films has become complex. While there is a considerable amount of knowledge available to a person of skill in this art, behaviors of polymers, or their properties under various physical conditions, such as machine stress and other conditions, are not readily understood. One might say the plastic film technology is, indeed, more of an art than a science and experience has proven that problems in this area of the art are not as easily understood or solved owing to the unknown factors in handling such polymeric compositions under machine stress either in the manufacture or fabrication of such polymers into useful articles.

U.S. Pat. No. 4,376,147 which issued in 1983 is directed to an embossed thermoplastic polyolefin film simulating a matte finish having excellent winding characteristics without edge curl, extremely low gloss even on both sides and good tape adhesion values, among other advantages, theretofore unachieved in prior matte films. In contradistinction to the prior art sand-blasted matte films, the film of the U.S. Pat. No. 4,376,147 has an embossed pattern comprising embossed lines or channel-like areas which are parallel to the free lengthwise edges of the film. The embossed lines provide a generally rectangular pattern with parallel and transverse lines numbering within the range of 150 to about 300 lines per inch. Employing such an embossed pattern, the surface of the film appears to the unaided eye as a very dull surface. Up to that point in the state of the art the matte film of the mentioned patent achieved a balance of physical surface characteristics theretofore unachieved in known matte films.

More recently, issued U.S. Pat. No. 4,546,029 is directed to a random embossed thermoplastic polyolefin film simulating a matte or dull finish having excellent roll or winding characteristics and processability without edge curl. Moreover, among its other important attributes, theretofore unachieved in prior art diaper matte films, it has relatively equal tape adhesion on both sides of the random embossed film. This is an important feature in diaper films which enables diapers to be used more effectively and conveniently without tearing the film. The random pattern comprises an asymmetric arrangement of asymmetrically raised bosses and depressed areas on one side of the film, and correspondingly, underlying asymmetrically depressed areas and raised bosses on the opposite side of the film. The asymmetric bosses and depressions are of such height and area on the surfaces of both sides of the film such that the unaided eye of an observer does not detect any pattern in the film, even though it is an embossed random pattern. Such a combination of design and embossed depth had been unachieved in plastic films and, quite surprisingly, a unique balance of physical properties had been obtained.

As evidenced by the above background, production of plastic film has been a continuously improving technology and there are demands for further innovation. There are particular demands for softer, more cloth-like film that eliminates the artificial effects normally associated with plastic.

SUMMARY OF THE INVENTION

This invention is directed to an ultra soft cloth-like embossed plastic film. In contrast to embossed plastic films heretofore produced, the films of this invention are extremely soft in their hand feel and quiet, thereby providing properties heretofore unachieved in the plastic film art.

The ultra soft cloth-like film of this invention has an embossed pattern and a plurality of post-embossed stretched areas along lines that are spaced uniformly across the surface areas on both sides of the embossed film. The stretched areas are separated by unstretched areas and the stretched areas have a thickness less than the unstretched areas of the embossed film. The inventive film is characterized by being ultra soft, cloth-like in texture and quiet when compared to the embossed film in its normal unstretched state.

In its most preferred form, the plurality of post-embossed stretched areas are spaced along lines at substantially uniform intervals completely across the width and the length of the plastic film. Preferably, these stretched areas are formed by intermeshing corrugated or gear-like rollers. It has not been heretofore known to stretch embossed plastic films to make them ultra soft, cloth-like and quiet. Furthermore, it has been found that new textures may be achieved in overcoming the artificial look of embossed films. The stretched areas along lines in the film may be continuous or discontinuous across the width or length of the film. The stretched lines may be spaced diagonally, perpendicularly or parallel to the length of the film, or in crossing patterns to such length. Thus, the film may be uniformly stretched along lines transverse to or along the length of the film, or along patterns across the length and the width of the film. These different stretched patterns may be achieved by providing multiple sets of stretching rollers either in line or in separate lines for diagonal, transverse or longitudinal stretching.

This invention is predicated in part upon the discovery that rather stiff and noisy embossed films may be made ultra soft, cloth-like and quiet. The ultra soft embossed plastic films of this invention eliminate the artificial appearance otherwise attributable to embossed plastic. Accordingly, this invention provides for a new dimension in embossed plastic films after several decades of their development as set forth in the background of this invention.

The films of this invention provide a barrier against liquid and yet have the appearance and feel of woven or non-woven fabrics. Alternatively, the films may be selectively perforated to meet the demands of breathable or permeable films. Furthermore, the post-embossed stretching methods according to this invention produce embossed films with textures and visible appearances heretofore unachieved in plastic films.

The most preferred films of this invention are relatively thin, particularly on the order of about 0.5 to about 2 mils. However, the advantages of this invention may be achieved in thicker films, on the order of up to 10 or more mils in thickness to provide such embossed films with a soft cloth-like hand feel and quiet properties. The depth of the emboss in thin films of about 0.5 to about 2 mils is well established in the art and usually ranges from about 1 to about 10 mils. However, in its broader aspects, this invention is not limited to these embossed depths, rather the ultra soft properties can be achieved with a wide variety of embossed depths and with many embossed patterns that are known to exist. For instance, the patents mentioned in the background of this invention disclose films having embossed patterns simulating woven taffeta, matte finishes and random patterns that may be stretched to provide the ultra soft, cloth-like and quiet properties. Each embossed pattern has raised bosses and surrounding depressions on one film side with substantially corresponding underlying depressions and bosses on the opposite side. Accordingly, the entire descriptions of the embossed patterns of U.S. Pat. Nos. 3,484,835; 4,376,147 and 4,546,029 are incorporated herein by reference so that a person of ordinary skill in the art may understand the types of embossed plastic films that may be provided with the ultra soft, quiet and other unique characteristics of this invention.

DETAILS OF THE INVENTION

The ultra soft cloth-like embossed film is made from any one of a number of suitable plastic materials, preferably of the thermoplastic type and particularly polyolefins including polyethylene, polypropylene, polybutadiene and copolymers of such polyolefins such as ethylene vinyl acetate, ethylene methyl acrylate and ethylene propylene diene monomer (EPDM). These polymers may be modified with conventional fillers, stabilizers, additives and the like. These film materials are embossed to give the nonwoven fibrous appearance for a number of applications including diapers, napkins and underpad applications as well as other medical disposable articles where the nonwoven appearance is desirable.

A preferred polyolefin film is ultralow, low density or medium density polyethylene. As is understood in the art, ultralow density polyethylene has a density of 0.890–0.912 with increasing density to 0.916 to 0.935 for low density polyethylene. Linear low density polyethylene having a density of 0.918 to 0.941 is also very suitable for use in accordance with this invention. Blends of the above ultralow density polyethylene, conventional high pressure polyethylene and low pressure linear low density polyethylene may be employed. For instance, 80% ultralow density polyethylene at a density of 0.912 may be blended with 20% high pressure low density polyethylene at a density of 0.922 with a blend density of approximately 0.914. From a formulation standpoint, to assist in achieving a soft and quiet product, the modulus, referred to as 1% secant modulus, of the formulated film may vary within the range of about 5,000 psi to 40,000 psi, with 5,000 psi to 20,000 psi preferred. For instance, polyethylene having a modulus in the range of about 5,000 psi to 20,000 psi provides for a soft, quiet and good hand-feel diaper. However, it is to be understood that the post-embossed stretched areas along lines across the width and length of the embossed film are responsible for the unique ultra soft, cloth-like and quiet properties of the inventive film.

As indicated above, embossed plastic film starting material may have any one of a number of embossed designs such as those disclosed in any one of the above-mentioned patents. A preferred method of making embossed patterns is also disclosed in these patents. The preferred method involves the introduction of thermoplastic material in a plastic state between a steel embossing roll and a smooth resilient roll or rubber roll which form a nip for embossing film. These techniques are considered to be conventional as described in the above mentioned patents that are embodied herein by reference.

The invention will be further understood with reference to the drawings in which.

Figure 1:
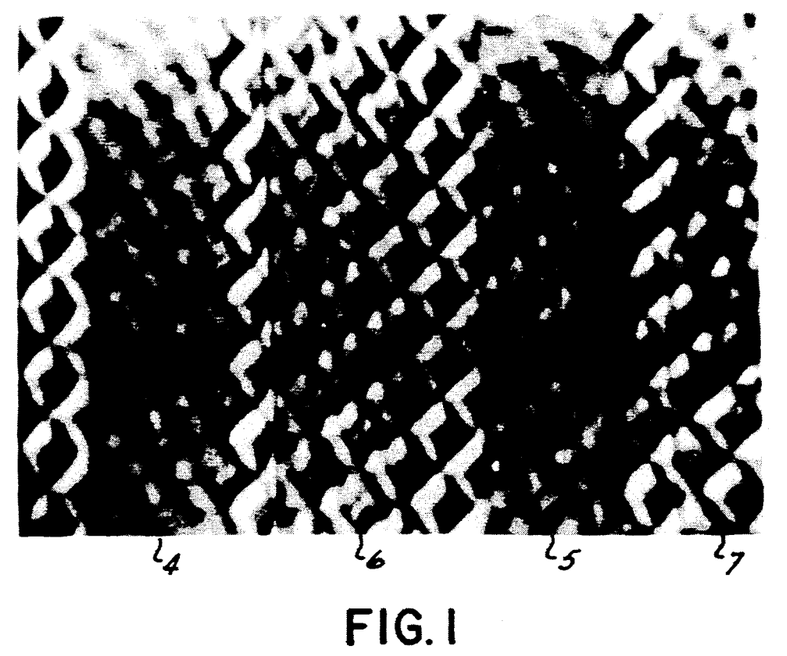
FIG. 1 is a magnified photographic partial view of an ultra soft embossed film of this invention having the embossed pattern disclosed in U.S. Pat. No. 3,484,835 that has been stretched with a plurality of post-embossed stretched areas along diagonal lines across its width and length. The sample was produced with a single pass through diagonal intermeshing stretching rollers, creating a pattern of alternating lines of stretched and unstretched areas. It is further described in the Table as Example 1.

With reference to the photograph of FIG. 1, a 1 mil polyethylene film is shown in top view that was embossed (steel embossing roller side) with a pattern simulating a woven taffeta design according to U.S. Pat. No. 3,484,835 and stretched according to this invention. The pattern, before stretching, comprises overall uniform bosses surrounded by channel-like areas overlying on the opposite side depressions and corresponding ridges as disclosed by the text of the '835 patent with reference to the figures. After the post-embossed stretching method of this invention, FIG. 1 demonstrates the key features of the stretched film in a partial view at about 18× magnification. The post-embossed stretched areas along lines 4, 5 diagonally across the width and length are separated by unstretched areas 6, 7 of the embossed film. In the stretched areas 4, 5 the embossed pattern has been dramatically altered due to the stretching of the film, while in the unstretched areas 6, 7, the original embossed pattern remains intact. The photograph was taken with the film sample in slight biaxial tension to remove puckers that are otherwise present in the relaxed film condition. The stretched areas have a thickness less than the thickness of the unstretched embossed film due to the thinning of the plastic in these areas. The film is characterized by being ultra soft, cloth-like and quiet when compared to starting embossed film in its normal unstretched state. The ultra soft stretched embossed film still is a liquid barrier. The underside of the FIG. 1 film is not shown but the underlying image corresponds to the negative of top side of the film with film thicknesses on the order of about 0.5 to 2 mils. In thicker films, the embossment is not necessarily imparted from one side to the other and the overlying and underlying areas may not substantially correspond. Nevertheless, it is to be understood that in thin films of about 0.5 to about 2 mils thickness, the top side pattern of the embossed film has a corresponding negative image on the underside of the film as is shown in the above-mentioned patent. It also should be understood that it is difficult to photograph and present the exact film structure due to the lighting, shadows and properties of plastic film as will be understood by a person of ordinary skill in this art. The embossed patterns are actually formed by an engraving roll having a distribution of depressions and raised areas simulating a desired pattern in a three-dimensional array. The process of engraving, master tooling and details thereof are not essential to this invention. The post-embossed stretching technique across the width and length of the embossed film will be described hereinafter to enable a person of ordinary skill in the art to produce the products of this invention.

Figure 2:
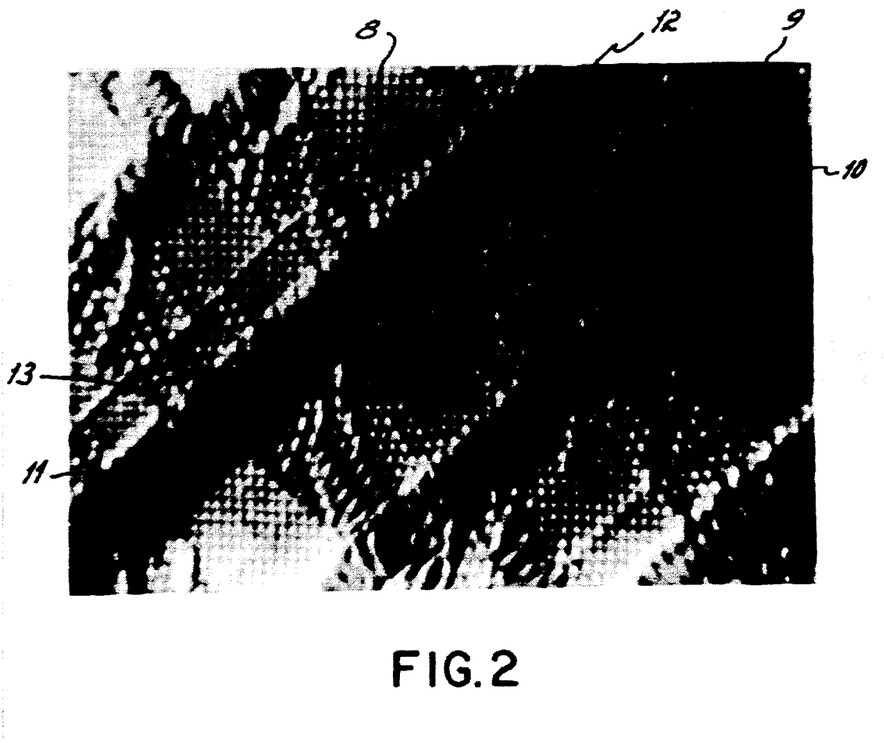
FIG. 2 is a magnified photographic partial view of an ultra soft embossed film of this invention having the embossed pattern disclosed in U.S. Pat. No. 4,376,147 that has been stretched with a plurality of post-embossed stretched areas along two crossing diagonal lines across its width and length. The sample was produced with two passes through diagonal intermeshing stretching rollers. After the first pass, the film was reversed, left for right for the second pass, creating a pattern of substantially perpendicular stretched lines diagonally oriented relative to the length and width of the film, and leaving some areas unstretched, some stretched once, and the remaining area stretched twice in a biaxial manner. It is further described in the Table as Example 2.

With reference to FIG. 2, a 1 mil polyethylene film is shown in top view that was embossed (steel embossing roller side) with a pattern simulating a woven matte finish according to U.S. Pat. No. 4,546,029 and stretched according to this invention. The pattern, before stretching, comprises overall uniform bosses surrounded by channel-like areas overlying on the opposite side depressions and corresponding ridges as disclosed by the text of the '029 patent with reference to the figures. After the post-embossed stretching method of this invention, in this example two passes through diagonal intermeshing stretching rollers with the stretching on the second pass perpendicular to the first pass, key features of the resultant film are shown in FIG. 2 at a magnification of about 18× and with the film under slight biaxial tension to remove puckers. Three distinct areas are shown: first, unstretched areas 8, 9; second, areas stretched once 10, 11; and third, stretched areas 12, 13 that were stretched twice. Stretched areas 12, 13 show the effect of the second pass stretching which occurred in a direction approximately 90° from the first pass stretching. The stretched areas 12, 13 are the thinnest areas of the film with stretched areas 10, 11 being thicker than stretched areas 12, 13 and thinner than unstretched areas 8, 9. Details of the stretched areas will be described later. The film is characterized by being ultra soft, cloth-like and quiet when compared to embossed film in its normal unstretched state. The ultra soft stretched embossed film still is a liquid barrier. The underside of the FIG. 2 film is not shown but the underlying image corresponds to the negative of top side of the film with film thicknesses on the order of about 0.5 to 2 mils.

Figure 3:
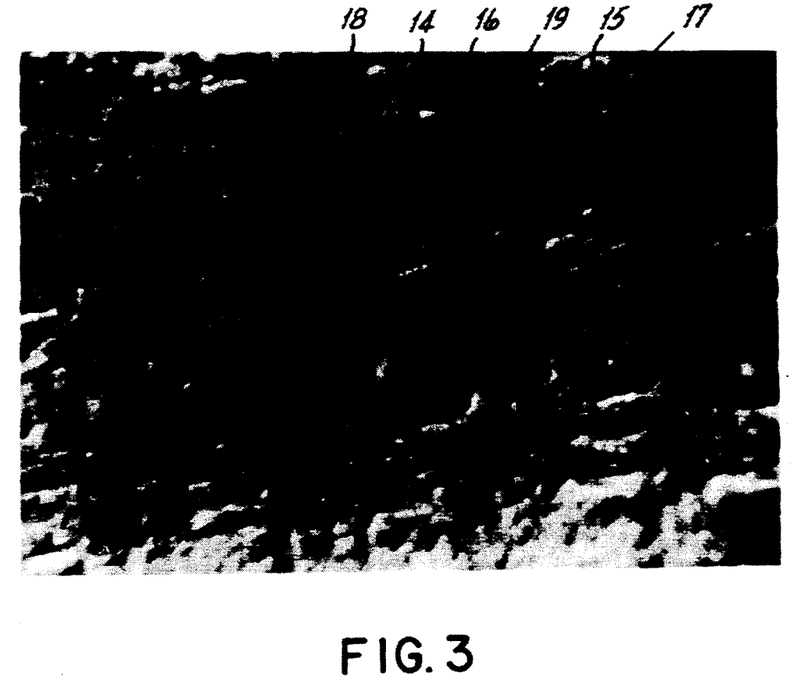
FIG. 3 is a magnified photographic partial view of an ultra soft embossed film of this invention having the embossed pattern disclosed in U.S. Pat. No. 4,546,029 that has been stretched with a plurality of post-embossed stretched areas along crossing lines across its width and length. The sample was produced with two passes through transverse direction intermeshing stretching rollers. After the first pass, the film was turned approximately 90° for the second pass, creating a pattern of substantially perpendicular stretched lines oriented parallel to the length and width of the film, and leaving some areas unstretched, some stretched once, and the remaining area stretched twice in a biaxial manner. It is further described in the Table as Example 4A.

With reference to FIG. 3, a 1 mil polyethylene film is shown in top view that was embossed with a pattern (rubber roller side) simulating a random embossed matte finish according to U.S. Pat. No. 3,484,835 and stretched according to this invention. The pattern, before stretching, comprised overall uniform bosses surrounded by channel-like areas overlying on the opposite side depressions and corresponding ridges with reference to the text and figures of this '835 patent. After the post-embossed stretching method of this invention, in this example two passes through transverse direction intermeshing stretching rollers with the film on the second pass turned approximately 90° relative to the first pass, key features of the resultant film are shown in FIG. 3 a magnification of about 18× and with the film under slight biaxial tension to remove puckers. Three distinct areas are shown: first, unstretched areas 14, 15; second, areas stretched once in the transverse direction 16, 17; and third, stretched areas 18, 19 stretched twice, once in the transverse direction and once in the longitudinal direction. As with the previously diagonally stretched sample, the unstretched areas 14, 15 retain the original thickness, once stretched areas 16, 17 are thinner than unstretched areas 14, 15 but thicker than twice stretched areas 18, 19. Again, details of the stretched areas will be described later. The film is characterized by being ultra soft, cloth-like and quiet when compared to embossed film in its normal unstretched state. The ultra soft stretched embossed film still is a liquid barrier. The underside of the film of FIG. 3 is not shown but the underlying image corresponds to the negative of top side of the film with film having a thicknesses on the order of about 0.5 to 2 mils.

In the above-mentioned description the term "embossed depth" is used and is determined by (a) measuring overall cross-sectional thickness (embossed gauge) of the film from the top side of the raised bosses to the opposite undermost ridges (or bosses) on the underside, (b) measuring or determining the average film thickness and subtracting (b) from (a). This measurement may be made in a number of manners. For instance, a standard 1 inch micrometer may be used in a manner known to those of ordinary skill in the art, to measure the embossed depth by measuring (a) and (b). For purposes of this invention, the film thickness may be calculated by determining the weight of a known area of the film and converting to thickness by knowing the film density. The embossed depth is the difference between the film embossed gauge as measured by a micrometer and the film thickness calculated on the basis of film density. The film embossed gauge is normally measured by a TMI Model 549M low load micrometer with a 2 inch diameter anvil.

The stretched embossed films as photographically shown in FIGS. 1-3 have a number of advantages. As stated, they are ultra soft and quiet. The films also simulate fabric, tissue or cloth in appearances and textures heretofore unachieved in embossed plastic films. These films may be processed advantageously and employed in diaper, napkin and underpad applications as well as other medical disposable articles where different appearances are desirable. Among other unique features, the films may have very low gloss on both sides. Films of this invention may be provided with woven, nonwoven and other unique appearances and still have an ultra soft hand-feel and a quiet property, i.e., they make little or no noise when crinkled.

In a preferred form of the invention, low to medium density polyethylene, for instance, is formed into a embossed film by a slot-die extrusion means. For example, the low to medium density polyethylene material is heated to a temperature of about 300°-500° F. and then introduced in a web form through a slot into the nip of a steel and rubber roll system referred to above. The plastic material, upon being introduced between the nip of the rolls, is film-formed and at the same time textured with the engraved pattern of the steel embossing roll. Under suitable embossing pressure, for instance of about 75-120 pounds per linear inch, a thin film having the embossed design may be produced. In achieving the preferred film thickness of between about 0.5-2 mils to about 10 mils, along with the necessary emboss depth of about 1 to about 10 mils, conditions are controlled in a manner well within the skill of those knowledgeable in the art of producing embossed films with the understanding of this invention. The factors which are considered may be varied depending upon the plastic material used and the characteristics to be obtained in the resultant film. Thus, process conditions that are obviously controlled to produce embossed film include temperature, pressure exerted between the nip of the embossing roll or system, the depth of the engraved design on the steel roll and the hardness of the rubber roll. Details are disclosed in the above referenced patents.

Other advantages and embodiments of this invention will be further understood with reference to the detailed operating examples and Table as follows.

The films of the examples are further identified in the following Table along with the conditions of stretching. All films were 1 mil in thickness except 6A which was 2.2 mils. Also "AIR" in the Table means the area increase ratio, i.e., the ratio of the stretched area (as encompassed by a circle scribed on the film after stretching) to the unstretched area (as encompassed by that same scribed circle before stretching). "SAR" means the stretched area ratio, i.e., the ratio of the width of stretched line to the width of the unstretched line. "NA" means not applicable. The composition, density, emboss, stretching, depth of stretch, speed and number of passes through the equipment are all indicated in Table. The embossing patterns are identified with reference to the trademarks that have been given for those patterns described in the above mentioned patents.

In the following examples diagonal intermeshing, cross direction (CD) intermeshing and machine direction (MD) intermeshing stretching was employed. These stretchers are described as follows:

A. Diagonal Intermeshing Stretcher

The diagonal intermeshing stretcher consists of a pair of left hand and right hand helical gear-like elements on parallel shafts. The shafts are disposed between two machine side plates, the lower shaft being located in fixed bearings and the upper shaft being located in bearings in vertically slidable members. The slidable members are adjustable in the vertical direction by wedge shaped elements operable by adjusting screws. Screwing the wedges out or in will move the vertically slidable member respectively down or up to further engage or disengage the gear-like teeth of the upper intermeshing roll with the lower intermeshing roll. Micrometers mounted to the side frames are operable to indicate the depth of engagement of the teeth of the intermeshing roll.

Air cylinders are employed to hold the slidable members in their lower engaged position firmly against the adjusting wedges to oppose the upward force exerted by the material being stretched. These cylinders may also be retracted to disengage the upper and lower intermeshing rolls from each other for purposes of threading material through the intermeshing equipment or in conjunction with a safety circuit which would open all machine nip points when activated.

A drive means is typically utilized to drive the stationary intermeshing roll. If the upper intermeshing roll is to be disengagable for purposes of machine threading or safety, it is preferable to use an antibacklash gearing arrangement between the upper and lower intermeshing rolls to assure that upon reengagement the teeth of one intermeshing roll always fall between the teeth of the other intermeshing roll and potentially damaging physical contact between addendums of intermeshing teeth is avoided. If the intermeshing rolls are to remain in constant engagement, the upper intermeshing roll typically need not be driven. Drive may be accomplished by the driven intermeshing roll through the material being stretched.

The intermeshing rolls closely resemble fine pitch helical gears. In the preferred embodiment, the rolls have 5.935" diameter, 45° helix angle, a 0.100" normal pitch, 30 diametral pitch, 14½° pressure angle, and are basically a long addendum topped gear. This produces a narrow, deep tooth profile which allows up to about 0.090" of intermeshing engagement and about 0.005" clearance on the sides of the tooth for material thickness. The teeth are not designed to transmit rotational torque and do not contact metal-to-metal in normal intermeshing stretching operation.

B. Cross Direction Intermeshing Stretcher

The CD intermeshing stretching equipment is identical to the diagonal intermeshing stretcher with differences in the design of the intermeshing rolls and other minor areas noted below. Since the CD intermeshing elements are capable of large engagement depths, it is important that the equipment incorporate a means of causing the shafts of the two intermeshing rolls to remain parallel when the top shaft is raising or lowering. This is necessary to assure that the teeth of one intermeshing roll always fall between the teeth of the other intermeshing roll and potentially damaging physical contact between intermeshing teeth is avoided. This parallel motion is assured by a rack and gear arrangement wherein a stationary gear rack is attached to each side frame in juxtaposition to the vertically slidable members. A shaft traverses the side frames and operates in a bearing in each of the vertically slidable members. A gear resides on each end of this shaft and operates in engagement with the racks to produce the desired parallel motion.

The drive for the CD intermeshing stretcher must operate both upper and lower intermeshing rolls except in the case of intermeshing stretching of materials with a relatively high coefficient of friction. The drive need not be antibacklash, however, because a small amount of machine direction misalignment or drive slippage will cause no problem. The reason for this will become evident with a description of the CD intermeshing elements.

The CD intermeshing elements are machined from solid material but can best be described as an alternating stack of two different diameter disks. In the preferred embodiment, the intermeshing disks would be 6" in diameter, 0.031" thick, and have a full radius on their edge. The spacer disks separating the intermeshing disks would be 5½" in diameter and 0.069" in thickness. Two rolls of this configuration would be able to be intermeshed up to 0.231" leaving 0.019" clearance for material on all sides. As with the diagonal intermeshing stretcher, this CD intermeshing element configuration would have a 0.100" pitch.

C. Machine Direction Intermeshing Stretcher

The MD intermeshing stretching equipment is identical to the diagonal intermeshing stretcher except for the design of the intermeshing rolls. The MD intermeshing rolls closely resemble fine pitch spur gears. In the preferred embodiment, the rolls have a 5.933" diameter, 0.100" pitch, 30 diametral pitch, 14¼° pressure angle, and are basically a long addendum, topped gear. A second pass was taken on these rolls with the gear hob offset 0.010" to provide a narrowed tooth with more clearance. With about 0.090" of engagement, this configuration will have about 0.010" clearance on the sides for material thickness.

OPERATING EXAMPLES

Example 1

The above described diagonal intermeshing stretcher was employed in this example to produce the incrementally stretched embossed plastic film that is photographically shown in FIG. 1. The woven taffeta plastic film of about 1 mil in thickness made in accordance with U.S. Pat. No. 3,484,835 was incrementally stretched using the diagonal intermeshing stretcher. The embossed plastic film initially was fairly stiff and noisy upon handling. Upon stretching with one pass through the diagonal intermeshing stretcher with a depth of roller engagement at about 0.085", post-embossed stretched areas 4, 5 appearing in FIG. 1 were obtained. The original emboss, with reference to FIG. 1 unstretched areas 6, 7, is mostly intact. It is believed that this happens as a result of the embossing process producing thick and thin areas in the original film. During the stretching process, the thin areas will stretch preferentially to the thick areas due to the lower resistance to the stretching force. Furthermore, it is believed that this type of stretching and the resultant structure impart some of the soft, cloth-like and quiet features to the film when compared with the normally unstretched embossed material. In addition, the stretching process increased the overall area of the film by about 44%. The area increase effected by diagonal stretching consists of dimensional increases in both the machine and cross direction.

Example 2

An embossed polyethylene film of about 1 mil in thickness was incrementally stretched in accordance with the method of this invention. The film was processed with the diagonal stretcher of Example 1 with two passes to provide crossing diagonal stretch lines and it is shown in magnified view in FIG. 2. The embossed film was made in accordance with U.S. Pat. No. 4,376,147 and had a matte finish attributable to the overall rectangular invisible pattern of channel-like areas surrounding bosses on one side with underlying depressions and ridges. The original embossed film was fairly stiff and noisy upon handling. After two passes through the diagonal intermeshing stretcher at a depth of 0.085", the film, reversed left for right for the second pass creating a pattern of substantially perpendicular stretched lines diagonally oriented relative to the length and width of the film, became very soft and quiet when handled. It had the appearance and feel like Kleenex facial tissue. The stretched film is shown in FIG. 2 with unstretched areas 8, 9, once stretched areas 10, 11 and twice stretched areas 12, 13.

Material may also be irregularly perforated using this technique if it does not have adequate elongation to survive the stretching in both directions. However, the degree of perforations can be controlled by controlling the depth of engagement and speed. With properly designed or formulated material, the diagonal intermeshing stretcher can produce perforated, texturized products with extreme softness.

Furthermore, in another variation, upon a single pass through the diagonal intermeshing stretcher, the embossed film of this example has a texture of corrugations with irregular puckers. In other words, the starting micro-embossed pattern had superimposed, by stretching, a texture of raised ribs and channels therebetween on both sides of the film. These corrugations give the film its texturized appearance and they also further account for its softness.

Example 3

In this example, the embossed film of Example 2 was run through the diagonal intermeshing stretcher and the rate of stretching was varied to determine the effects. During the course of these experiments the film was also prewrapped about 150° around the initial roller and the speeds of 55, 130 and 200 fpm were employed. At 55 fpm, the incrementally stretched material had a uniform corduroy pattern much like that of Example 1 with characteristic puckering in the unstretched areas of stretching (See 3A of Table). At 130 fpm, the appearance of the film was similar but with perhaps 100 perforations/sq. ft (See 3B of Table). The sample run at 200 fpm was full of holes (See 3C of Table). In some cases, the adjacent holes were connected and were more like tears. This example demonstrated the rate of stretch is an important factor at least for this particular polyethylene blend.

Example 4A

For this example, an intermeshing stretcher device was employed to incrementally stretch an embossed film of the random embossed type described in U.S. Pat. No. 4,546,029 in the cross and machine directions. For comparison with the diagonal intermeshing stretcher of Examples 1-3, the pitch of the CD stretcher was 0.100" as is the normal pitch of the diagonal unit. The CD depth was set to about 0.085" to simulate the diagonal stretcher at its practical maximum depth. Under these conditions, the embossed films of this example were run through the unit at about 200 fpm and the effects achieved by Example 2 was similarly achieved in the CD stretcher. In other words, running an embossed film through the stretcher in a perpendicular direction produced a deeply uniformly corrugated appearance of incremental stretching caused by the transverse alternating ribs and channels across the film. In addition, the films stretched in this manner had the characteristic ultra soft, cloth-like and quiet properties.

These properties are in large part due to the following reasons. As intermeshing stretching is done, puckers are formed in the lines of unstretched material. These puckers are a result of a contraction in the stretched material in a direction perpendicular to the direction of stretch. This effect is easily demonstrated by taking a strip of plastic film that is, for example, 1" wide and 6" long and stretching it lengthwise to increase the 6" dimension. As this is done, the 1" dimension will be decreased. Any unstretched portion of the strip will thus remain wider than any stretched portion. The puckers result because the lines of unstretched material are inherently longer than the lines of stretched material and the excess length accumulates as fairly regular bistable billows which irregularly project above or below the plane of the stretched material. When touching the material, one first encounters these billows or puckers of unstretched, embossed film since they project above and below the stretched film. These unstretched, embossed areas are also under virtually zero tension since any of the tensions created by lightly handling the film manifest themselves first on the stretched lines. A retained random emboss in the unstretched area together with the easily deformable pucker shape in the stretched area provide the very dry, soft feel of the film. The stretched areas, having a substantially reduced thickness due to the stretching are very flexible and act as hinges allowing the bulk material to flex as if it were all as thin as the thinnest areas, adding to the softness, quietness, and fabric-like drapability of the film.

Example 4B

Further experiments were performed with the CD stretcher by changing the depth of the engagement of the elements from 0.085 to about 0.235" (See 4B of Table). Upon doing so, a 7" wide piece of random embossed 1 mil film entering the stretcher left at about 26" wide. The film was very soft, very thin and very clingy and not obviously puckered as previous films made in accordance with Examples 1 and 2, for instance. The films employed to produce this effect were polyethylene blends. The materials previously stretched at a depth of 0.085" and identified had a stretched area ratio (SAR) of less than 1. The SAR is the ratio of the width of the stretched line to the width of the unstretched line. The material of this Example 4B has an SAR of almost 9 indicating that the unstretched line is very narrow relative to the stretched line. The stretched area is also very thin being about 1/5 the thickness of the unstretched area by actual measurement. A highly stretched film having a SAR of nearly 9 tends to feel very soft because its puckered, unstretched lines occupy only about 1/9 of its surface area and are not effective in preventing the stretched area from contacting the observers skin. The stretched area, because of its extreme thinness, flexibility and virtual lack of emboss conforms very well to the fine details of any surface it contacts, and thus has a clingy feel. Films produced in accordance with this example having high SAR values, typically greater than 4, that are stretched in the CD or MD, as well as both CD and MD are ultra-soft and quiet, but may tend to be clingy in hand feel instead of dry and, thus, less cloth-like.

Example 5

Random embossed film of Example 4 (U.S. Pat. No. 4,546,029) was also incrementally stretched employing the diagonal intermeshing stretcher of Examples 1-3. Using a 1 mil film, the sample was produced with two passes through diagonal intermeshing stretching rollers with an engagement of about 0.085". After the first pass, the film was reversed left for right for the second pass, creating a pattern of substantially perpendicular stretched lines diagonally oriented relative to the length and width of the film similar to Example 2. The resulting film was ultra-soft, quiet, and cloth-like.

Comparing this Example 5 with Example 4A, the properties of ultra-softness, quietness and cloth-like texture and hand feel are achievable by either diagonal or CD/MD intermeshing stretching means. Comparing this Example 5 with Example 2, the effects of the double pass diagonal intermeshing stretching process can be differentiated from the effects of original embossing pattern and material composition. Both samples achieved ultra-soft, quiet, and cloth-like characteristics. For instance, the random embossed film of this Example 5 retained the characteristic sparkle and feel of the original embossed material even after stretching.

Example 6

Polyethylene films on the order of about 1 mil in thickness and having visibly embossed patterns such as linen or non-woven fibrous character were incrementally stretched using a diagonal intermeshing stretcher technique in accordance with the previous examples (See 6A and 6B of Table). It has been found that the post-embossed stretched film dramatically breaks up the gloss or plastic-like effect associated with these known patterns and forms products that are soft and sparkling. The overall gloss of the normal embossed film is broken up into randomized facets so that only a small percentage can thus reflect light in any one direction at one time. Furthermore, due to the incrementally stretched areas that break up the embossed pattern, these otherwise stiff films are rendered ultra soft. Varying degrees of stretching over the SAR values of about 1 to about 9 significantly increase the usable area of the films. Even though these types of films have been stretched, the embossed patterns are still evident when the surfaces are viewed either by the naked eye or microscopically. Thus, this invention offers unique and unexpected results in producing plastic substitutes for woven and non-woven substrates giving the texture of such materials with an ultra soft hand.

TABLE

| Example | Film | | | Stretching | | | | | |
|---------|------|---|---|---|---|---|---|---|---|
| | Composition | Density | Emboss | Type | Depth | Speed | Passes | AIR | SAR |
| 1 | 80% LDPE<br>20% LLDPE | .925 | Taff-A-Flex* | Diag. | 0.085" | 200 fpm | 1 | 1.44 | 2.40 |
| 2 | 72% LLDPE<br>28% LDPE | .936 | Microflex* | Diag. | 0.085" | 50 fpm | 2 | 1.99 | NA |
| 3A | 72% LLDPE<br>28% LDPE | .936 | Microflex | Diag. | 0.085" | 55 fpm | 1 | 1.51 | .61 |
| 3B | 72% LLDPE<br>28% LDPE | .936 | Microflex | Diag. | 0.085" | 130 fpm | 1 | 1.50 | .81 |
| 3C | 72% LLDPE<br>28% LDPE | .936 | Microflex | Diag. | 0.085" | 200 fpm | 1 | 1.52 | .69 |
| 4A | 80% ULDPE<br>20% LDPE | .914 | Sof-flex* | CD/MD | 0.085" | 200 fpm | 2 | 1.71 | NA |
| 4B | 80% ULDPE<br>20% LDPE | .914 | Sof-flex | CD | 0.235" | 100 fpm | 1 | 3.54 | 8.9 |
| 5 | 80% ULDPE<br>20% LDPE | .914 | Sof-flex | Diag. | 0.085" | 200 fpm | 2 | 1.37 | 2.55 |
| 6A | 100% LLDPE | .920 | Linen | Diag. | 0.085" | 200 fpm | 2 | 1.41 | NA |
| 6B | 80% ULDPE<br>20% LDPE | .914 | Nonwoven | Diag. | 0.085" | 200 fpm | 2 | 1.38 | NA |

*Taff-A-Flex, Microflex and Sof-flex are trademarked products of Clopay Corporation Having described the above invention and its preferred parameters, various modifications may be made as understood by a person of ordinary skill in this art in view of this specification.

What is claimed is:

1. An ultra soft embossed plastic film suitable for use as a cloth or fabric having the appearance and feel of non-woven or woven fabric and having liquid barrier properties comprising:
   a thermoplastic film selected from the group consisting of polyethylene, polypropylene and copolymers thereof having a thickness on the order of about 0.5 to about 10 mils and a pattern embossed therein in its normal unstretched state having thick and thin areas and a plurality of post-embossed stretched areas along lines spaced substantially uniformly across the surface areas on both sides of the embossed film, said stretched areas being separated by unstretched areas and having a thickness less than the unstretched areas, said thin areas of said embossed plastic film in its normal unstretched state being stretched preferentially to the thick areas due to the lower resistance to the stretching force, said film being ultra soft and quiet when used as a cloth or fabric upon comparison with the embossed plastic film in its normal unstretched state.

2. The film of claim 1 for use as a liquid barrier.

3. The film of claim 1 further comprising perforations in the stretched areas.

4. The film of claim 1 wherein said stretched areas provide said embossed film with a visible texture of raised ribs and channels therebetween caused by stretching on both sides of the film.

5. The film of claim 4 wherein said ribs and channels extend substantially continuously diagonally to the free edges of the film.

6. The film of claim 4 wherein said ribs and channels extend substantially continuously and perpendicularly to the free edges of said film.

7. The film of claim 4 wherein said ribs and channels extend substantially continuously and parallel to the free edges of the film.

8. The film of claim 1 embossed with a pattern selected from the group consisting of woven fabric, non-woven fabric and matte finish.

9. The film of claim 1 embossed with a pattern of raised bosses surrounded by substantially perpendicularly intersecting channels on one side of the film overlying on the opposite side corresponding depressions and perpendicularly intersecting ridges.

10. The film of claim 1 embossed with a pattern of irregularly shaped bosses surrounded by irregularly shaped channels on one side of the film overlying on the opposite side corresponding irregularly shaped depressions and irregularly shaped ridges.

11. An ultra soft embossed plastic film suitable for use as a cloth or fabric having the appearance and feel of non-woven or woven fabric and having liquid barrier properties comprising:
   an embossed thermoplastic film selected from the group consisting of polyethylene, polypropylene and copolymers thereof having a thickness on the order of about 0.5 to about 10 mils and a pattern in its normal unstretched state having thick and thin areas of raised bosses and depressions on one side of the film overlying on the opposite side of the film corresponding depressions and bosses, said pattern selected from the group consisting of woven fabric, non-woven fabric and matte finish,
   said film having a plurality of post-embossed stretched areas along lines that are spaced substantially uniformly and completely across the surface areas on both sides of the film, said stretched areas being separated by unstretched areas of said embossed pattern and said stretched areas having a thickness less than the unstretched areas, said thin areas of said embossed plastic film in its normal unstretched state being stretched preferentially to the thick areas due to the lower resistance to the stretching force, said film being ultra soft and quiet when used as a cloth or fabric upon comparison with said embossed film in its normal unstretched state.

12. The film of claim 11 having an embossed depth of from about 1 to about 10 mils.

13. The film of claim 12 wherein said thickness is from about 0.5 to about 2 mils and said embossed pattern depth is from about 1 to about 10 mils.

14. The film of claim 11 wherein said thermoplastic is selected from the group consisting of ultra low, low and medium density polyethylene.

* * * * *